US010478366B2

(12) United States Patent
Hettich (10) Patent No.: US 10,478,366 B2
(45) Date of Patent: Nov. 19, 2019

(54) ADJUSTABLE ORTHOSTATIC INTOLERANCE SYSTEM AND GARMENT

(71) Applicant: Mary Ann Hettich, Matthews, NC (US)

(72) Inventor: Mary Ann Hettich, Matthews, NC (US)

(73) Assignee: BSN Medical, Inc., Charlotte, NC (US)

( * ) Notice: Subject to any disclaimer, the term of this patent is extended or adjusted under 35 U.S.C. 154(b) by 243 days.

(21) Appl. No.: 14/220,339

(22) Filed: Mar. 20, 2014

(65) Prior Publication Data
US 2014/0207034 A1    Jul. 24, 2014

Related U.S. Application Data

(63) Continuation of application No. 13/075,739, filed on Mar. 30, 2011, now abandoned.

(51) Int. Cl.
| | | |
|---|---|---|
| *A61H 1/00* | (2006.01) | |
| *A41B 11/14* | (2006.01) | |
| *A41D 13/00* | (2006.01) | |
| *A61F 13/08* | (2006.01) | |
| *A61F 13/14* | (2006.01) | |

(52) U.S. Cl.
CPC ............. *A61H 1/008* (2013.01); *A41B 11/14* (2013.01); *A41D 13/0015* (2013.01); *A61F 13/08* (2013.01); *A61F 13/148* (2013.01); *A41B 2400/32* (2013.01)

(58) Field of Classification Search
CPC ........ A61F 13/08; A61F 13/06; A61F 13/143; A61F 5/02; A61F 5/03; D04B 1/265; D04B 1/24; D10B 2501/021; A41B 11/14; A41B 11/143; A41B 11/146; A41B 11/08
USPC ..................... 602/62, 75, 60, 53, 76; 601/84
See application file for complete search history.

(56) References Cited

U.S. PATENT DOCUMENTS

| | | | | |
|---|---|---|---|---|
| 2,370,754 A * | 3/1945 | Roseman | ................ | A41F 1/006 24/588.12 |
| 4,368,546 A * | 1/1983 | White | .................... | A41B 11/14 2/239 |
| 5,315,716 A * | 5/1994 | Baum | ....................... | A41D 1/06 2/114 |
| 6,296,618 B1 * | 10/2001 | Gaber | ................... | A61F 13/143 24/442 |
| 2010/0170026 A1 * | 7/2010 | Jeffords | ................... | A41D 1/06 2/227 |

FOREIGN PATENT DOCUMENTS

FR          2915851 A1 *  11/2008  ......... A41D 13/0015

* cited by examiner

*Primary Examiner* — Ophelia A Hawthorne
*Assistant Examiner* — Caitlin A Carreiro
(74) *Attorney, Agent, or Firm* — Shumaker, Loop & Kendrick, LLP (57) ABSTRACT

An adjustable orthostatic intolerance garment formed of a knitted spandex powernet construction in order to provide compression when on the leg, and including legs and a torso portion that extends upwardly into the abdominal area below the pectoral muscles; and a respective pair of elongate panels that are retained in place by attaching elements, and that are introduced into or removed from the garment to increase or reduce compression on the wearer's body as desired.

12 Claims, 8 Drawing Sheets

ADJUSTABLE ORTHOSTATIC INTOLERANCE SYSTEM AND GARMENT

CROSS-REFERENCE TO RELATED APPLICATION

This application is a continuation application of U.S. application having Ser. No. 13/075,739 filed on Mar. 30, 2011, which is a non-provisional application claiming priority to U.S. Provisional Application having Ser. No. 61/319,084 filed on Mar. 30, 2010. This application expressly incorporates by reference the entire disclosure of and claims the entire benefit of both the Ser. No. 13/075,739 non-provisional application and also the 61/319,084 provisional application.

TECHNICAL FIELD AND BACKGROUND OF THE INVENTION

During extended periods of exposure to a gravity free environment such as experienced by astronauts, the body's fluids redistribute in response to the weightless environment. This fluid change triggers responses in the autonomic nervous and cardiovascular systems which, when coupled with low humidity conditions in space vehicles, results in progressive fluid volume loss and symptoms associated with dehydration. This is called "orthostatic intolerance." Attempts have been made to resolve these problems upon return to Earth by applying various types of compression garments to the astronauts upon return to Earth. However, prior efforts have been limited by variation in the amount of fluid volume loss from astronaut to astronaut, so that in some cases the compression garments were so loose that they did not function adequately.

To counter the effects of orthostatic intolerance upon return to earth's gravitational force, it has been determined that it is desirable to use a "gradient compression garment," and to maintain a desired compression profile even with dimensional changes in the body. The primary areas of concern are the upper thigh and abdomen.

A second need is to provide a means of gradually returning the astronauts back to normal gravitational exposure. To accomplish this, it is proposed to provide a means in which the compression level can be incrementally reduced.

There are multiple advantages that the system described below provides over current garments and garment system. First, the system may serve to adjust the compressive force (fabric tension) over areas of the body most susceptible to volume loss during extended exposure to a non-gravity environment. Second, the system may provide precise adjustments of the garment to ensure a continuous applied pressure gradient, being highest at the ankle and decreasing proximally. Third, the system may permit gradually reintroducing the astronaut to normal gravitational forces upon return to earth after extended stays in weightlessness. Fourth, the system may apply compression to the wearer promptly after re-entry into a gravity environment without the need for an air supply or electrical power for pumps or other pressure-inducing means.

SUMMARY OF THE INVENTION

Therefore, a system that includes one, two or three inter-related garments and hosiery products has been developed that improves adjustment of astronauts to the effect of gravity on the fluid retention and placement in the body.

A 3-piece system consisting of two thigh length supports (one for each leg) of a non-standard compression profile (~55 mmHg at the ankle and gradually decreasing to ~23 mmHg at the thigh), and a garment that extends above the waist to just below the pectorals and approximately to mid-thigh on both legs. The garment includes a tapered panel inserted on either side that extends along the entire length of the body and ends at the thigh circumference.

The degree of taper and the width of the panel are configured such as to provide ±2 mmHg to a body that may experience up to 4 cm of circumferential change. The garment may include multiple tapered inserts, or panels, that are adjacent to one another on either or both sides of the body. Thigh extensions are designed to be worn over the upper portion of the thigh length support described above, and the combination of which maintains a gradient compression profile.

One embodiment of the garment includes a double wall abdominal panel that extends from the pubis to the top of the support. The double panel is made from the same body fabric and is intended to provide additional extension resistance and support over the abdominal fluid reservoir. In one embodiment, elastic bands are attached to the lower ends that form around the thigh and at the top of the garment. Tabs are attached to affect continuity of the elastic loops after zipper closure.

Thigh length supports are also adapted to include enclosed zippers that are inserted on the medial aspect of the garment extending distally from the base of the gastrocnemius to the medial malleolus.

One embodiment of the invention is a 3-piece system having two thigh length supports (one for each leg) of a non-standard compression profile (~55 mmHg at the ankle and gradually decreasing to ~23 mmHg at the thigh), and a garment that extends above the waist to just below the pectorals and approximately to mid thigh on both legs.

An adjustable means on either side of the garment extends along the entire length of the body and ends at the thigh circumference. The adjustable mechanism(s) are attached to the elastic body fabric in such a manner as to pull the fabric to a higher tension and the brief to a reduced circumference. The degree of width adjustment/tightening of the body fabric is configured such as to provide ±2 mmHg to a body that may experience up to 4 cm of circumferential change.

A garment is also proposed in which the adjustable mechanism is interlacing and a means for discretely cinching them, such as by the BOA Lacing system that enables lacings to be tightened or loosened in discrete increments by rotating a knob in the desired direction.

Alternatively, the adjustable mechanism may be a series of hooks and eyes.

Another alternative construction is a garment in which the adjustable mechanism is hook and loop type fasteners upon which specific gradations or landmarks have been applied to identify specific degrees of tightening.

In a further alternative construction, the adjustable mechanism is a series of full length separating zippers spaced in defined increments.

In one embodiment, a garment includes thigh extensions designed to be worn over the upper portion of the thigh length support, the combination of which maintains a gradient compression profile.

A further embodiment includes elastic bands attached to the lower ends that form around the thigh and at the top of the garment. Tabs are attached to affect continuity of the elastic loops after zipper closure.

A system of compression garments provides a non-standard compression profile (~55 mmHg at the ankle and gradually decreasing to ~23 mmHg at the thigh), and a garment that extends above the waist to just below the pectorals and approximately to mid thigh on both legs.

One embodiment includes a knee high "liner" sock providing ~15 mmHg at the ankle and an open-toe thigh length over stocking that provides ~40 mmHg at the ankle.

BRIEF DESCRIPTION OF THE DRAWINGS

Some of the objects of the invention have been set forth above. Other objects and advantages of the invention will appear as the description of the invention proceeds when taken in conjunction with the following drawings, in which.

DESCRIPTION OF THE PREFERRED
EMBODIMENTS AND BEST MODE

Figure 1:
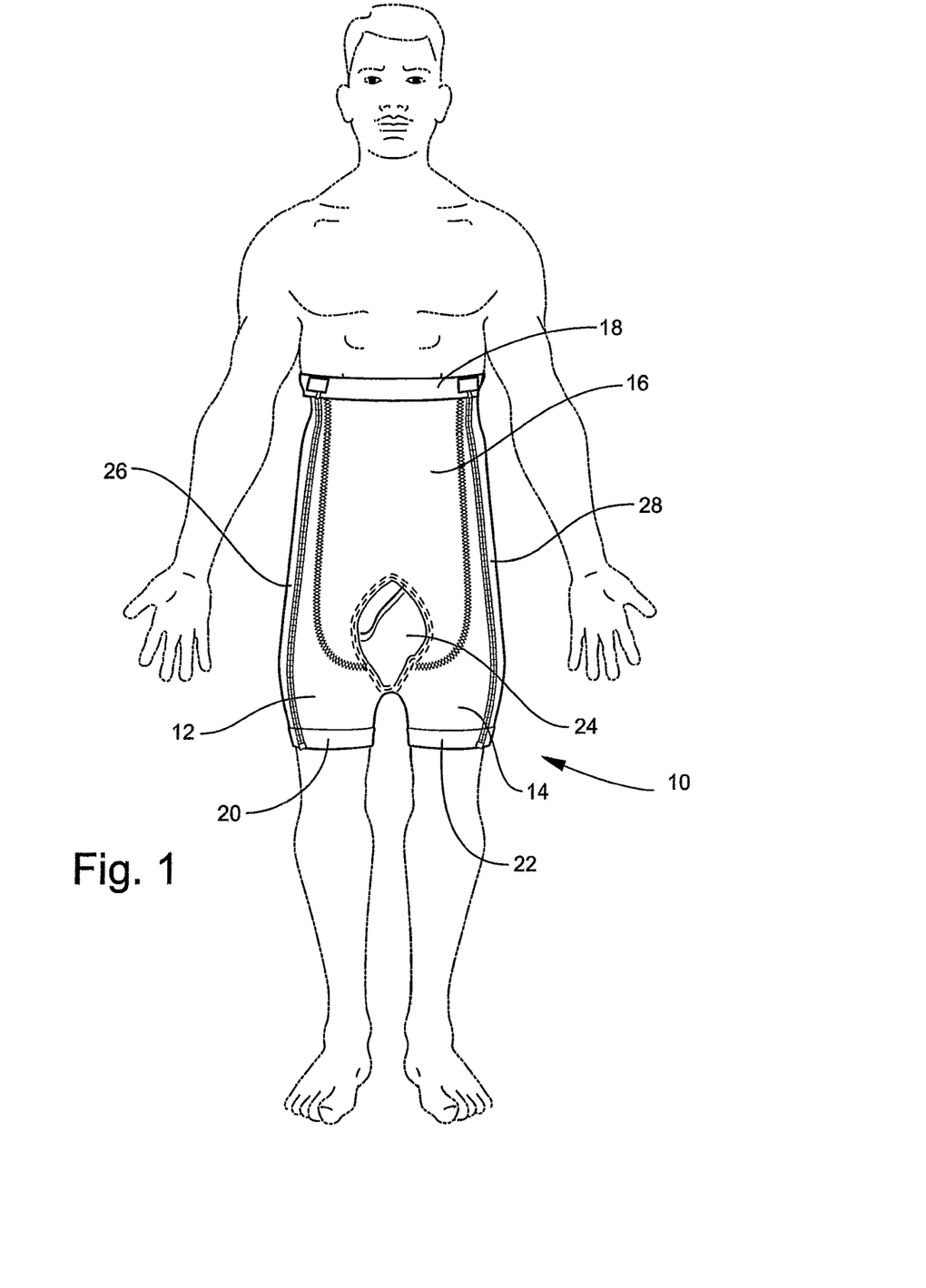
FIG. 1 is an overall view of an adjustable orthostatic intolerance garment system according to one embodiment of the invention in position on a human body.

Referring now specifically to the drawings, an adjustable orthostatic intolerance garment system according to one embodiment of the invention in position on a human body is shown generally in FIG. 1 at reference numeral 10.

Figure 2:
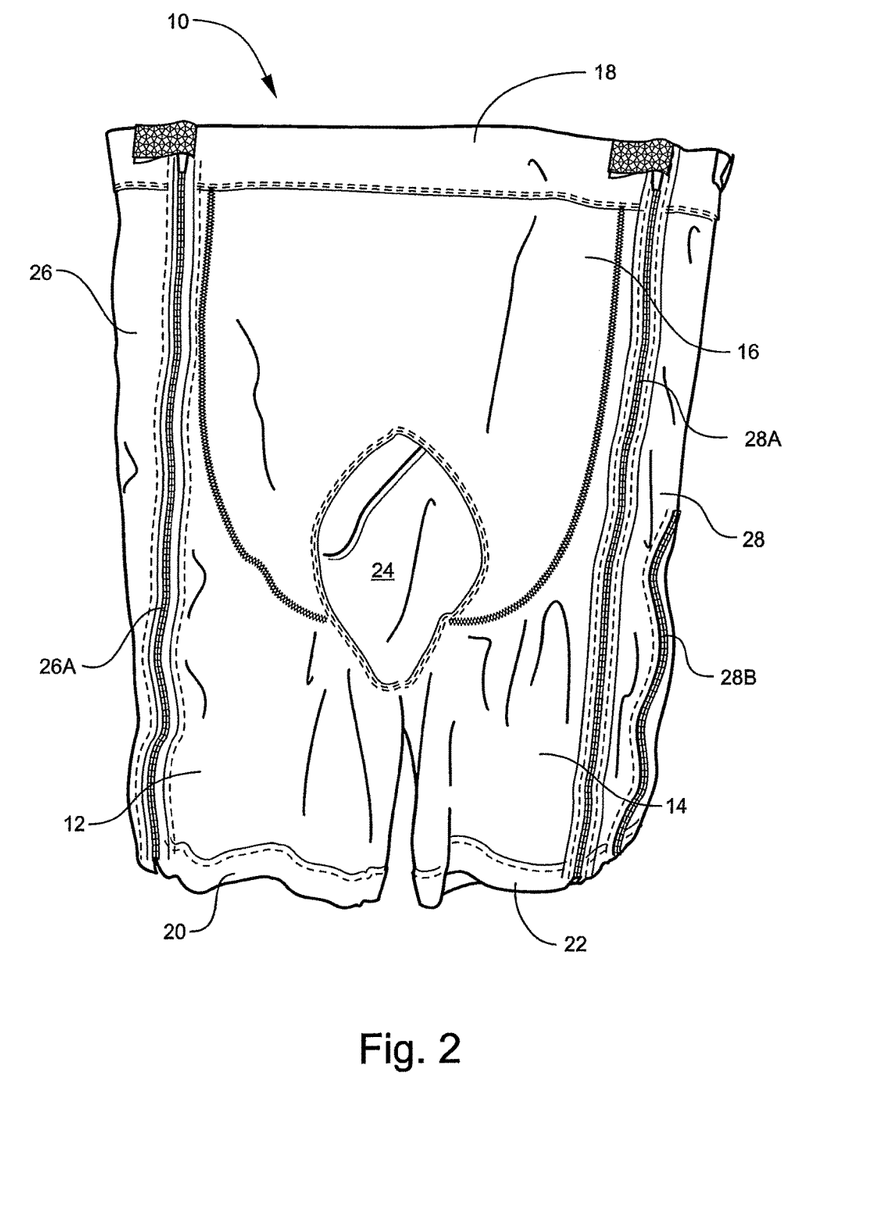
FIG. 2 illustrates an embodiment of a body an adjustable orthostatic intolerance garment according to one embodiment of the invention.
Figure 3:
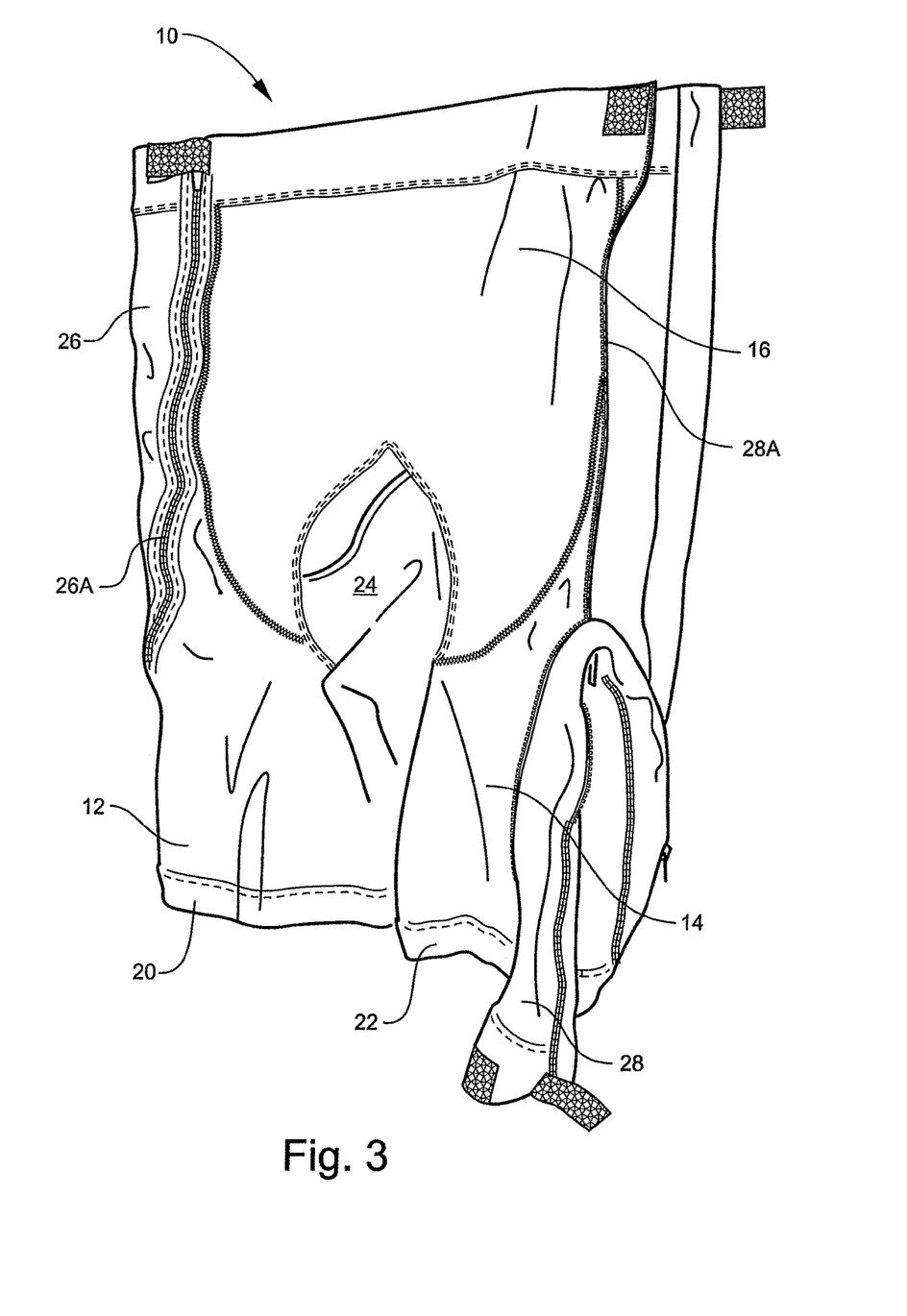
FIG. 3 illustrates another embodiment of a body an adjustable orthostatic intolerance garment according to one embodiment of the invention.

As is shown more specifically in FIGS. 2 and 3, the garment 10 as generally illustrated in FIG. 1 is formed of a knitted spandex powernet construction using either 840 or 1120 Denier spandex yarns in order to provide pressure of about 55 mmHg when in place on the leg. The garment 10 includes legs 12, 14, and a torso portion 16 that extends upwardly into the abdominal area below the pectoral muscles. The garment 10 includes an elastic band 18 at the upper end and elastic bands 20, 22 at each leg bottom to prevent the legs 12, 14 from riding up the thigh. A fly 24 for use when worn by a male, or a flap (not shown) for use when worn by a female, is provided. In the particular embodiment shown in FIGS. 2 and 3, and best shown in FIG. 3, legs 12, 14 include a respective pair of elongate tapered panels 26, 28 that are retained in place by zippers, as is best shown in FIG. 3, where the panel 28 is shown partially unzipped from zippers 28A, 28B. Panel 26 is retained on the garment 10 and removed by complementary zippers 26A, and 26B (26B not shown).

When initially donned by a wearer suffering from fluid loss, the garment 10 is used without the panels 26, 28, and the zippers 26A, 26B and 28A, 28B are zipped together. As fluid is replaced in the wearer, the wearer may be given additional room with essentially the same or similar compression gradient by inserting the panels 26, 28 into the garment 10. This is accomplished by unzipping the zippers 26A, 26B and 28A, 28B, and attaching the panel to the garment with complementary zipper components carried by the panel.

Figure 4:
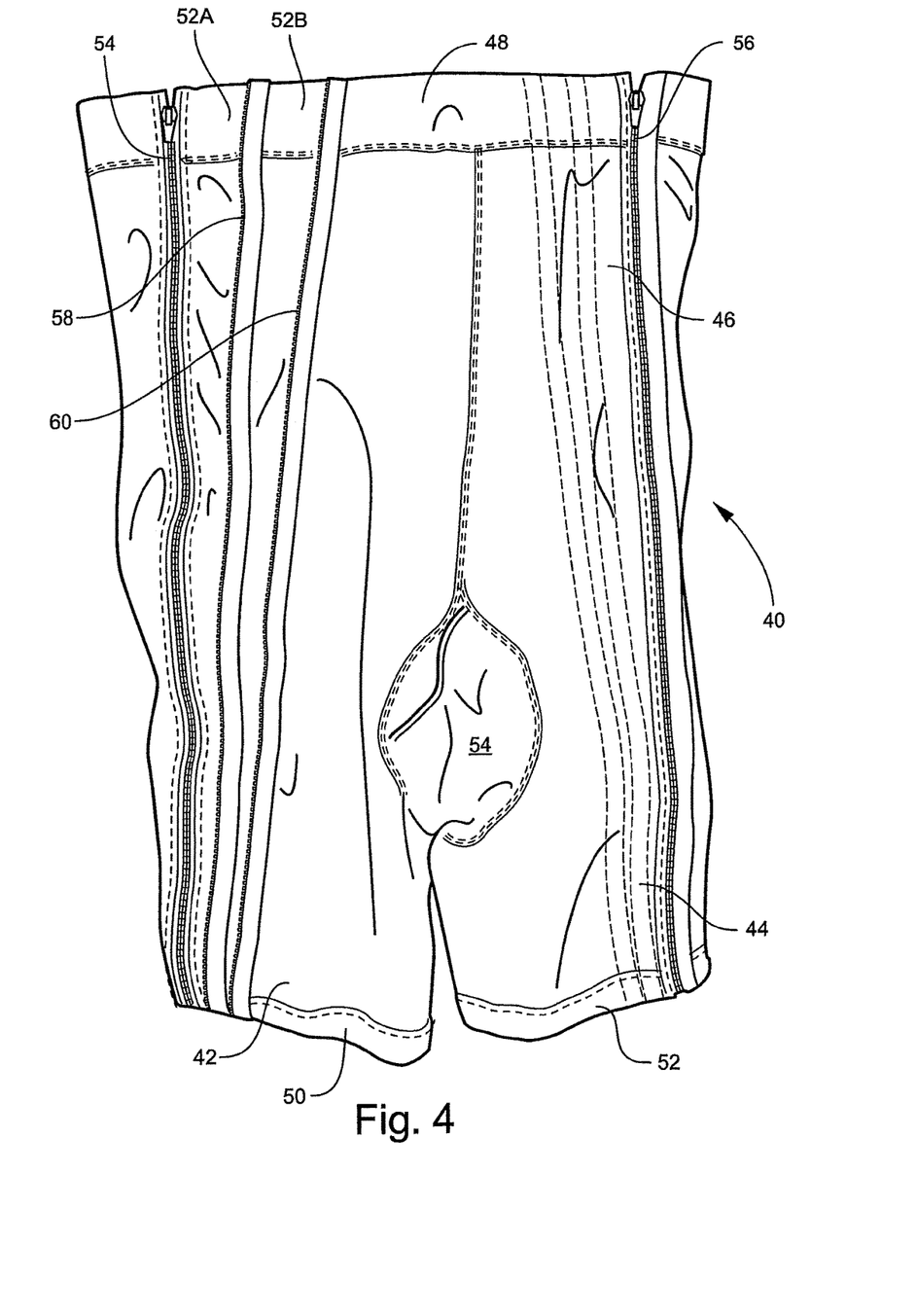
FIG. 4 illustrates another embodiment of a body an adjustable orthostatic intolerance garment according to one embodiment of the invention.

Referring now to FIG. 4, the garment 40 is formed of a knitted spandex powernet construction using either 840 or 1120 Denier spandex yarns in order to provide pressure of about 55 mm Hg. when in place on the leg. The garment 40 includes legs 42, 44, and a torso portion 46 that extends upwardly into the abdominal area below the pectoral muscles. The garment 40 includes an elastic band 48 at the upper end and elastic bands 50, 52 at each leg bottom to prevent the legs 42, 44 from riding up the thigh. A fly for a male wearer or a flap (not shown) for use when worn by a female, is provided. In the particular embodiment shown in FIG. 4 legs 42, 44 include respective pairs of elongate tapered panels. Panels 52A, 52B, on the right side of the garment 40 is shown in FIG. 4. Identical panels are present, but not shown, on the left side of the garment 40. Zippers 54 and 56 extend the entire length of the garment 40 from the top to the bottom along the distal aspect of the thighs. Each side of the garment 40 may include a pair of additional zipper elements, such as zipper elements 58, 60 shown in the right side of the garment 40, or all of the size adjustment may be obtained by adjustments of the right side of the garment 40.

When initially donned by a wearer suffering from fluid loss, the garment 40 is used with the zipper 54 connected to the proximal zipper element 60, substantially as shown on the right side of the garment 40. As fluid is replaced in the wearer, the wearer may be given additional room with essentially the same or similar compression gradient by attaching the zipper 54 to the zipper element 58, and finally to position shown in FIG. 4. As noted above, all of the adjustment may be carried out with zipper 54, or a like adjustment may be made on the left hand side as well.

Figure 5:
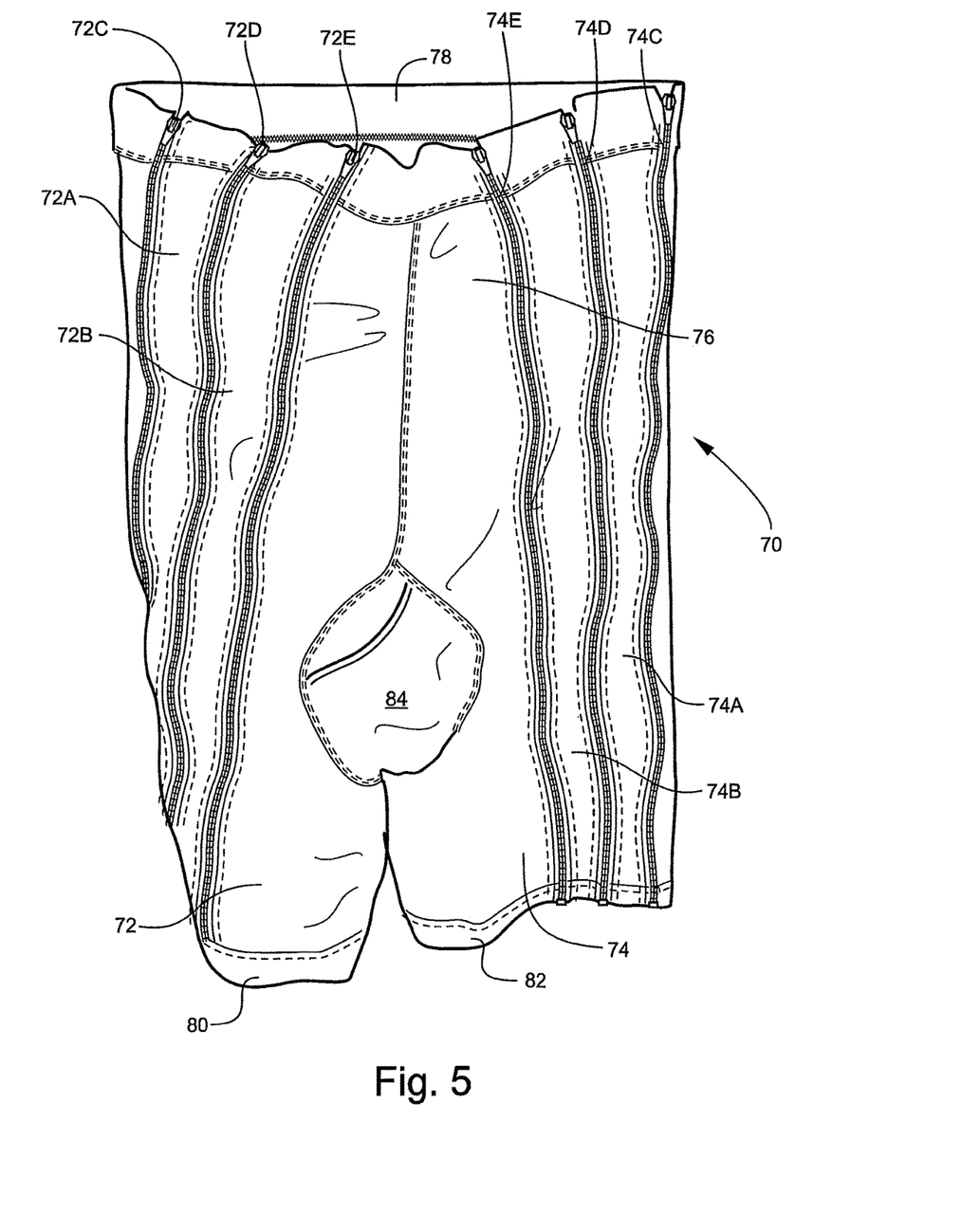
FIG. 5 illustrates another embodiment of a body an adjustable orthostatic intolerance garment according to one embodiment of the invention.

Referring now to FIG. 5, the garment 70 is formed of a knitted spandex powernet construction using either 840 or 1120 Denier spandex yarns in order to provide pressure of about 55 mm Hg. when in place on the leg. The garment 70 includes legs 72, 74, and a torso portion 76 that extends upwardly into the abdominal area below the pectoral muscles. The garment 70 includes an elastic band 78 at the upper end and elastic bands 80, 82 at each leg bottom to prevent the legs 72, 74 from riding up the thigh. A fly 84 for male use or a flap (not shown) for use when worn by a female, is provided. In the particular embodiment shown in FIG. 5, legs 72, 74 each include a respective pair of elongate tapered panels 72A, 72B, 74A, 74B, that are retained in place by zippers 72C, D and E, and 74C, D and E.

When initially donned by a wearer suffering from fluid loss, the garment 70 is used without the panels 72A, 72B, 74A, 74B and the zippers 72C and 72E, and 74C and 74E are zipped together. As fluid is replaced in the wearer, the wearer may be given additional room with essentially the same or similar compression gradient by inserting the panels 72A and 74A into the garment 70. This is accomplished by unzipping the zippers and attaching the panels 72A, 74A to the garment 70 with the complementary zipper components, as shown. Finally, the panels 72B and 74B may likewise be inserted, in the same manner as described above.

Figure 6:
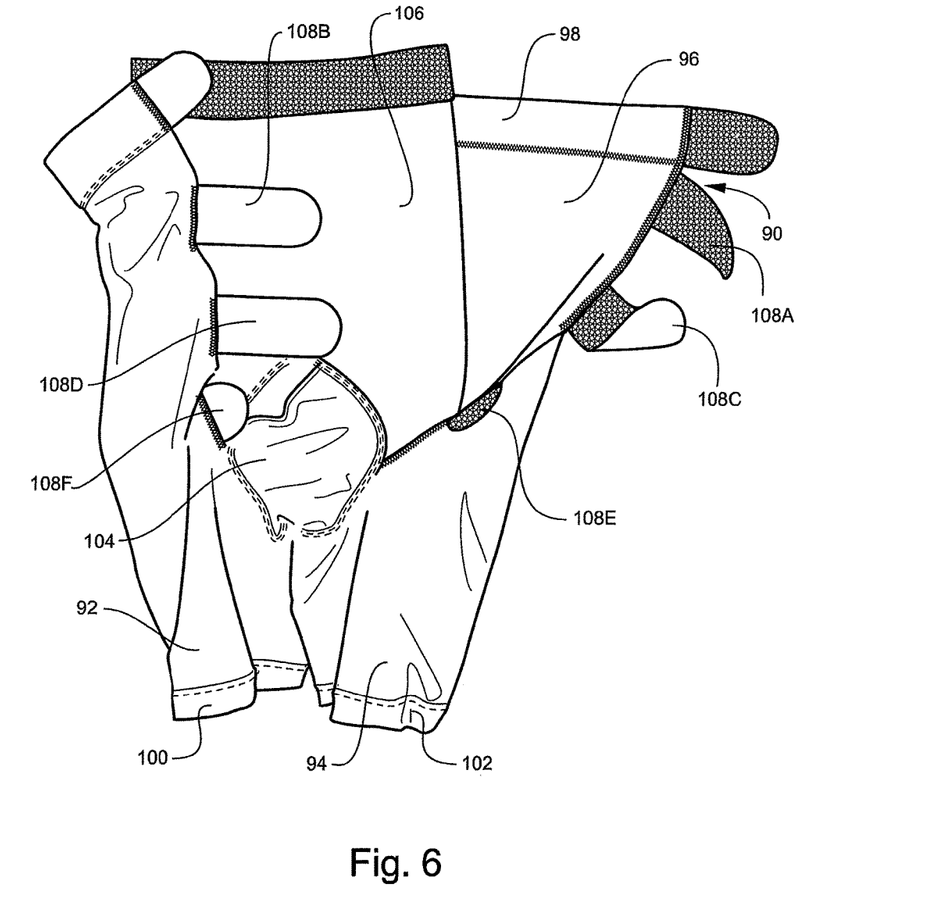
FIGS. 6 and 7 illustrate yet another embodiment of a body an adjustable orthostatic intolerance garment according to one embodiment of the invention.
Figure 7:
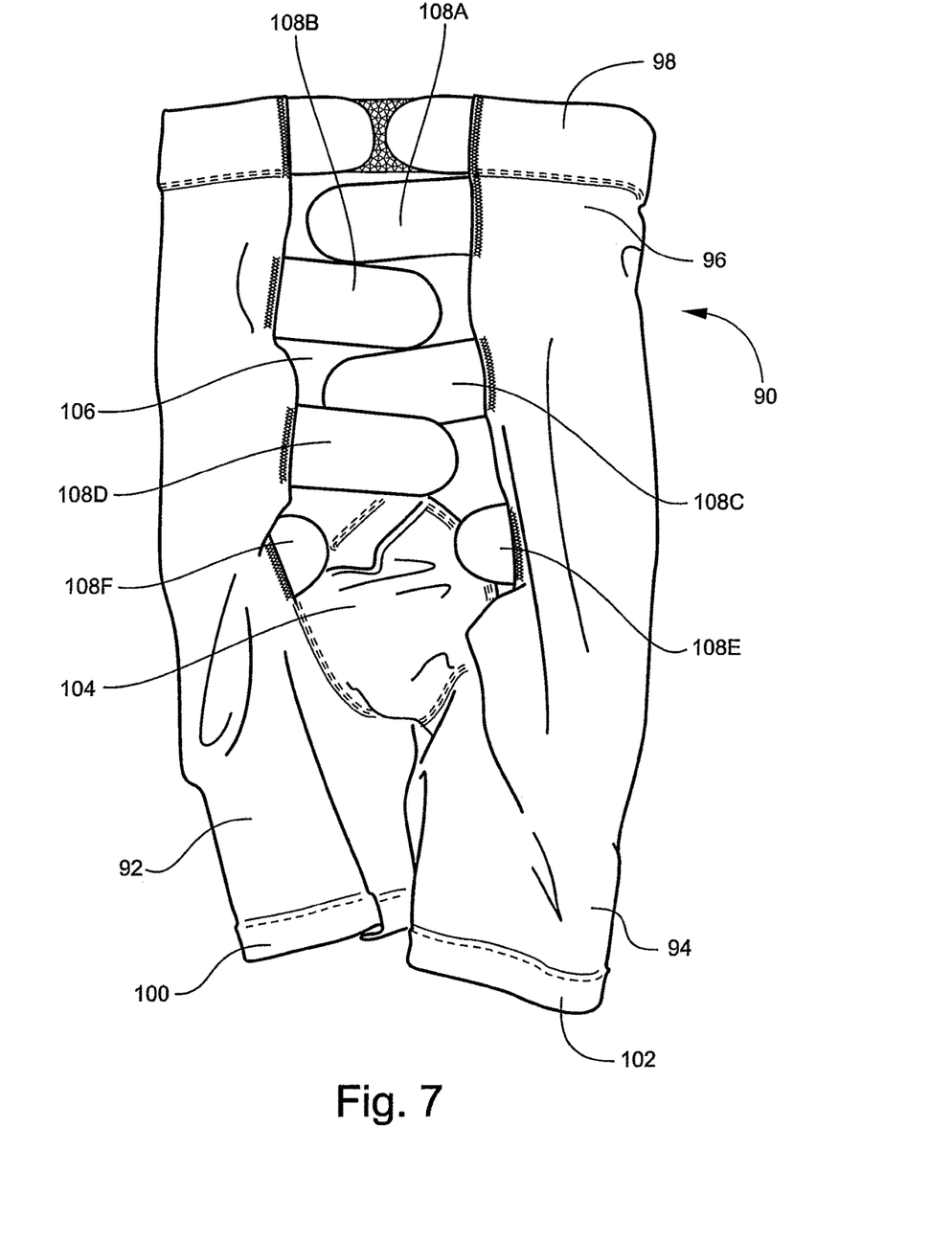

Referring now to FIGS. 6 and 7, another embodiment of an adjustable orthostatic intolerance garment is shown at reference numeral 90 that is formed of a knitted spandex powernet construction using either 840 or 1120 Denier spandex yarns in order to provide pressure of about 55 mm Hg. when in place on the leg. The garment 90 includes legs 92, 94 and a torso portion 96 that extends upwardly into the abdominal area below the pectoral muscles. The garment 90 includes an elastic band 98 at the upper end and elastic bands 100, 102 at each leg bottom to prevent the legs 92, 94 from riding up the thigh. A fly 104 for a male wearer or a flap (not shown) for use when worn by a female, is provided. In the particular embodiment shown in FIG. 6, the garment 90 includes a central panel 106 of a inelastic material having a fibrous surface adapted for being releasably engaged with complementary hooks of a conventional hook and loop system. The panel 106 is attached by stitching to the garment 90 on the bottom edge in the area of the fly 104, but is not attached on either side, and is freely moveable side-to-side as necessary for adjustment. The garment 90 includes opposing sets of adjustment straps 108 A-F that extend inwardly from opposing distal sides of the garment 90. The inward sides of the straps 108A-F are covered with hook-type touch fasteners that grip the fibrous surface of the panel 106 when pressed onto its surface. Thus, adjustment takes place by determining the correct compression to be applied to the wearer with the adjustment straps 108A-F in a released condition, and then pressing the straps 108A-F against the panel 106 to fix the compression at the desired level. The correct position of the straps 108A-F may be determined by markings applied to the garment indicating the approximate location of the straps 108A-F on the panel 106, or by other means.

With each of the embodiments described in this application, various methods of adjusting the compression of the garments may be used. For example, hook and loop systems, hook and eye systems, and criss-cross lacing systems (i.e., such as BOA devices with an adjustment knob that is turned for loosening or tightening the laces) may be used in lieu of and/or in combination with zippers.

Figure 8:
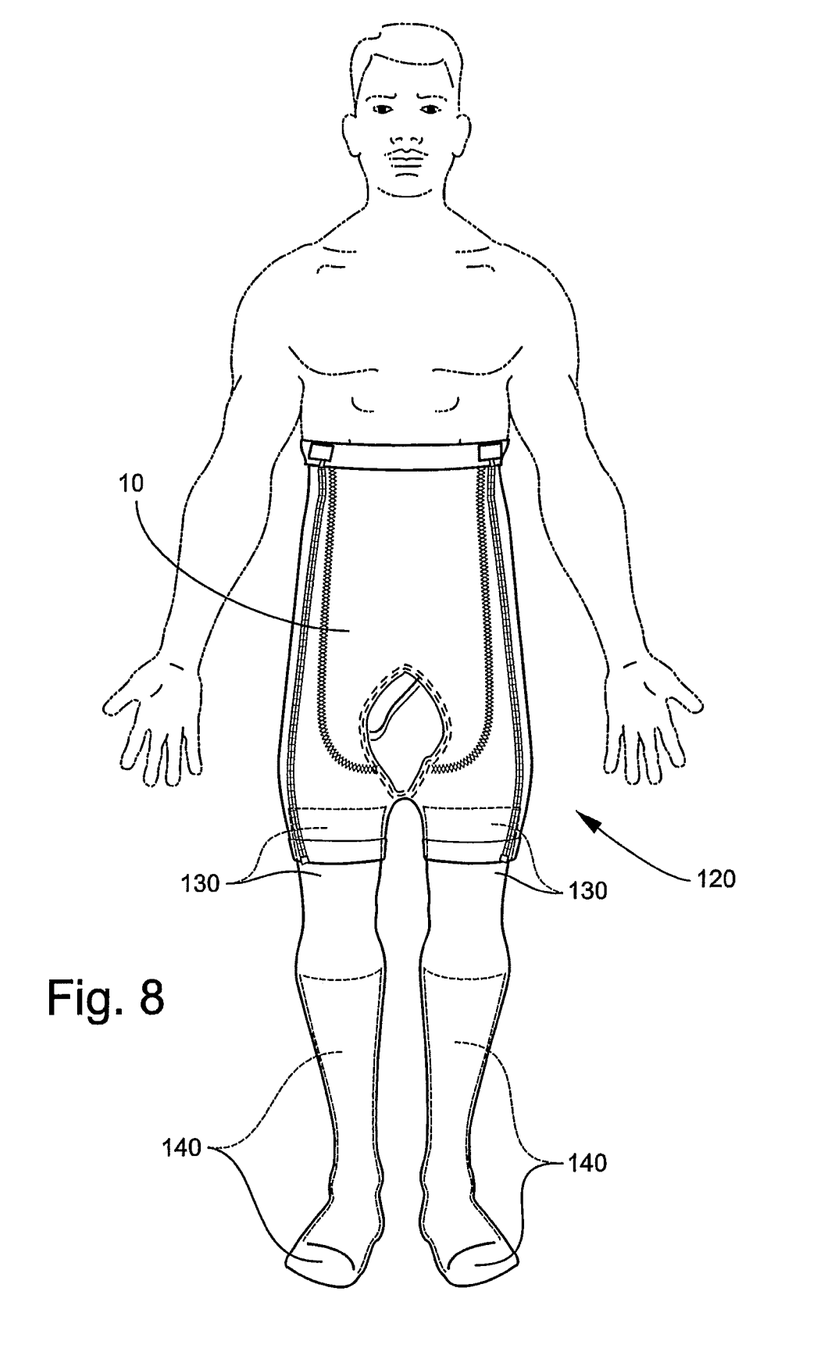
FIG. 8 illustrates an embodiment that incorporates with an adjustable orthostatic intolerance garment according to one embodiment of the invention other compression elements on the legs and feet of the wearer to form an adjustable orthostatic intolerance system.

Referring now to FIG. 8, an adjustable orthostatic intolerance garment according to one embodiment of the invention is combined with other compression elements on the legs and feet of the wearer to form an adjustable orthostatic intolerance system 120. For purposes of illustration, the garment 10 described above is shown, it being understood that any of the garments described in this application, whether or not illustrated, can be used as part of the system 120. Compression stockings 130 are worn In combination with the garment 10 to provide additional compression on the leg, and to prevent the garment 10 from causing pooling of fluids in the lower extremity. The basic construction of the compression stockings 130 is similar to that of the garment 10, i.e., a powernet construction of knitted spandex yarns of a predetermined suitable denier, as described above, or another suitable denier. As shown, the compression stockings 130 extend from the foot, have an open toe, and terminate on the upper thighs of the wearer a few inches above the bottom of the legs of the garment 10 so that there is an overlap of several inches on the legs.

Optionally, a liner sock 140 can be worn under the compression stockings 130. The liner socks 140 are preferably knitted of nylon, silk, or a combination of these or other flat yarns, and provide a low-friction surface to aid in donning the compression stockings 130. The liner socks 140 may also be treated with anti-microbial agents to reduce odor. Typically, the liner socks would extend upwardly to the calves of the wearer, as shown in FIG. 8, but may be either longer or shorter.

An adjustable orthostatic intolerance garment and garment system is described above. Various details of the invention may be changed without departing from the scope of the invention. Furthermore, the foregoing description of the preferred embodiment of the invention and best mode for practicing the invention are provided for the purpose of illustration only and not for the purpose of limitation, the invention being defined by the claims.

What is claimed is:

1. An adjustable orthostatic intolerance garment, comprising:
   (a) two leg portions and a torso portion constructed of a knitted compression fabric, the leg portions each having lateral portions configured to extend along an outer thigh and opposing medial portions configured to extend along an inner thigh and the torso portion configured to extend upwardly from the leg portions into the abdominal area and below the pectoral muscles;
   (b) a pair of elongate openings, each continuously extending along the lateral portions of one of the leg portions and each defined by adjacent side edges of the fabric extending from an uppermost extent of the torso portion to a lowermost extent of a respective one of the leg portions and adapted to be releasably connected together by attachment elements continuous along an entire length of the garment extending from an outermost end portion of the torso portion of the garment to an outermost end portion of each leg portion of the garment to provide the legs and the torso with openings sized to provide a predetermined volume and an upwardly directed pressure gradient to the body of the wearer;
   (c) a pair of removable elongate fabric panels adapted for insertion into a respective one of the pair of elongate openings, each fabric panel having panel side edges with complementary attachment elements continuous along an entire length of each fabric panel for being attached to the attachment elements continuous on adjacent side edges of the fabric of the elongate openings along the entire length of the torso portion and the leg portions to form the torso and leg portions with a volume that is greater than the volume provided when joined directly together, the volume comprising an upwardly directed pressure gradient configured for a wearer whose dimensional profile has changed as a result of fluid redistribution during a prolonged stay in a zero gravity environment; and
   (d) a pair of knitted compression stockings adapted to extend upwardly along the legs and overlap with the lowermost extent of the leg portions for providing a pressure gradient directed upwardly from the feet of the wearer;
   wherein the pair of removable elongate fabric panels when inserted into the respective one of the pair of elongate openings do not overlap the leg and torso portions;
   wherein each removable elongate fabric panel includes a plurality of attachment elements, each attachment element of the plurality of attachment elements is parallel relative to one another and continuously extends on the longitudinal axis of the elongate fabric panel to selectively vary leg portion circumference of the adjustable orthostatic intolerance garment to provide the desired upwardly directed pressure gradient; and wherein a continuous pressure gradient is highest at an ankle of the wearer and decreases progressively towards the uppermost extent of the torso portion.

2. An adjustable orthostatic intolerance garment according to claim 1, wherein the adjacent side edges of the fabric forming the elongate opening define a taper extending from the uppermost extent of the torso to the lowermost extent of the leg portions.

3. An adjustable orthostatic intolerance garment according to claim 2, wherein the taper narrows from top to bottom.

4. An adjustable orthostatic intolerance garment according to claim 1, wherein the torso portion includes an abdominal panel extending from a pubis area of the garment to an upper portion of the torso portion.

5. An adjustable orthostatic intolerance garment according to claim 1, and including at least one elastic band attached around the respective lowermost extent of the leg portions and the uppermost extent of the torso portion.

6. An adjustable orthostatic intolerance garment according to claim 1, wherein the garment has a knitted spandex powernet construction.

7. An adjustable orthostatic intolerance garment according to claim 1, and including a second pair of elongate fabric panels for being inserted into the elongate openings together with the pair of elongate fabric panels to provide a further increase in volume selected to a desired a upwardly directed pressure gradient.

8. An adjustable orthostatic intolerance garment according to claim 1, wherein the pair of elongate fabric panels is constructed of a knitted compression fabric.

9. An adjustable orthostatic intolerance garment according to claim 1, wherein the pair of elongate fabric panels is constructed of a knitted spandex powernet fabric.

10. An adjustable orthostatic intolerance garment according to claim 1, wherein the each attachment element of the plurality of attachment elements is a zipper.

11. An adjustable orthostatic intolerance garment according to claim 1, and including a pair of low-friction liner socks for being worn beneath the compression stockings to aid in donning the compression stockings.

12. An adjustable orthostatic intolerance garment according to claim 1, wherein a compression profile of each of the two leg portions includes a pressure of 55 mmHg at the wearer's ankle and a pressure of 23 mmHg at the wearer's thigh.

* * * * *